United States Patent [19]
Gordon

[11] Patent Number: 5,300,075
[45] Date of Patent: Apr. 5, 1994

[54] COVER FOR ORTHOPEDIC SPLINTING RODS AND METHOD OF INSTALLATION

[76] Inventor: Donn M. Gordon, 230 Craig Rd., Neshanic Station, N.J. 08853

[21] Appl. No.: 762,314

[22] Filed: Sep. 18, 1991

[51] Int. Cl.$^5$ .............................................. A61B 17/00
[52] U.S. Cl. .................................... 606/72; 606/53
[58] Field of Search ............... 606/53, 72, 73; 411/61, 411/377, 431, 57, 60; 439/825, 753

[56] References Cited

U.S. PATENT DOCUMENTS

| D. 321,401 | 11/1991 | Scanlan et al. | D24/147 |
|---|---|---|---|
| 2,175,759 | 10/1939 | Olson | 439/825 |
| 2,517,677 | 8/1950 | Kjell-Berger et al. | 439/825 X |
| 2,699,535 | 1/1955 | Flora | 439/825 X |
| 2,851,670 | 9/1958 | Senior | 439/825 |
| 3,809,075 | 5/1974 | Matles | 606/72 |
| 3,852,704 | 12/1974 | Muz | 439/825 |
| 3,969,976 | 7/1976 | Amico | 411/61 |
| 4,408,372 | 10/1983 | Kimura et al. | 411/61 X |
| 4,688,560 | 8/1987 | Schultz | 606/73 |
| 4,883,399 | 11/1989 | MacLean | 411/431 |
| 4,968,202 | 11/1990 | Lanham | 411/377 X |
| 4,976,712 | 12/1990 | VanderSlik | 606/59 |

FOREIGN PATENT DOCUMENTS

| 0587046 | 10/1933 | Fed. Rep. of Germany | 439/825 |
| 2432862 | 3/1980 | France | 606/72 |

OTHER PUBLICATIONS

J.B.J.S., vol. XX, No. 3, p. 781, Jul. 1938.

*Primary Examiner*—Robert A. Hafer
*Assistant Examiner*—Brian E. Hanlon
*Attorney, Agent, or Firm*—Weingram & Zall

[57] ABSTRACT

The present invention sets forth a cover for orthopedic splinting rods which in its broadest sense consists of a single sheet of material which is formed into a cylinder having a longitudinal slit up its side and a curved top of the cap to allow for natural resilience of the cap to hold the walls of the cap against the edges of the ends of the splinting rods to insure retention of the cap on the ends of the splinting rods. An embodiment for external use encases the metal cap in a plastic housing having a gripping means to assist in the installation of the cap on the ends of the splinting rod. The external housing has smooth surfaces to avoid and minimize any trauma to surrounding body tissue. The present invention also sets forth a method of installing a cover for orthopedic splinting rods on the clipped end of the rod, comprising the steps of rotating of the metal cap down over the burred end of the clipped splinting rods and rotating the cap to cause the burred end of the cap to form a helical groove or type of screw thread in the wall of the cap to secure the cap. The cap tapers at the end near the top so as to cause ever increasing pressure on the burred end of the splinting rod as it is advanced into the cap.

22 Claims, 5 Drawing Sheets

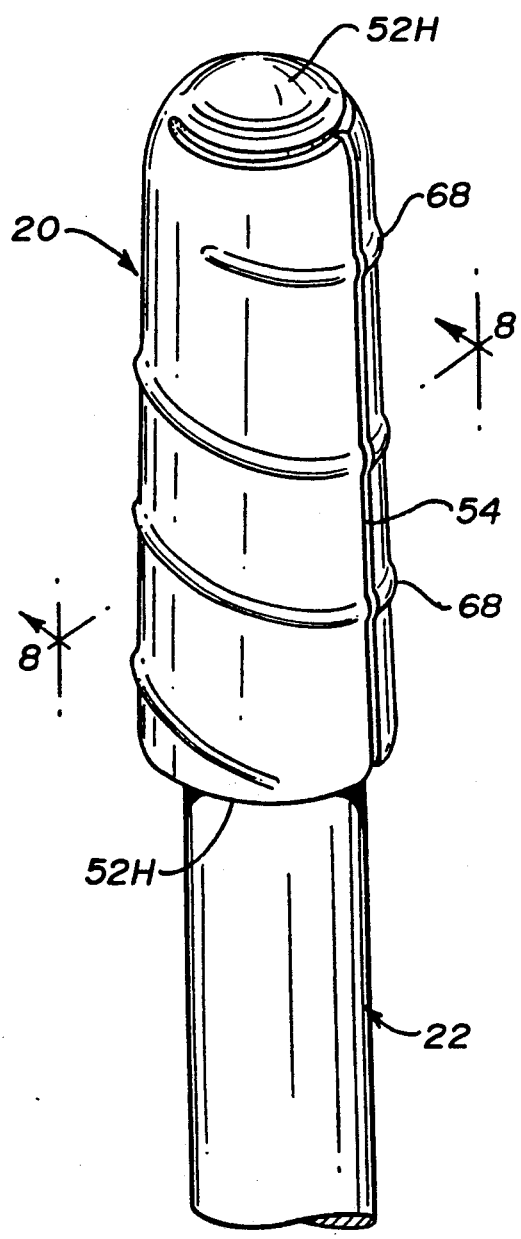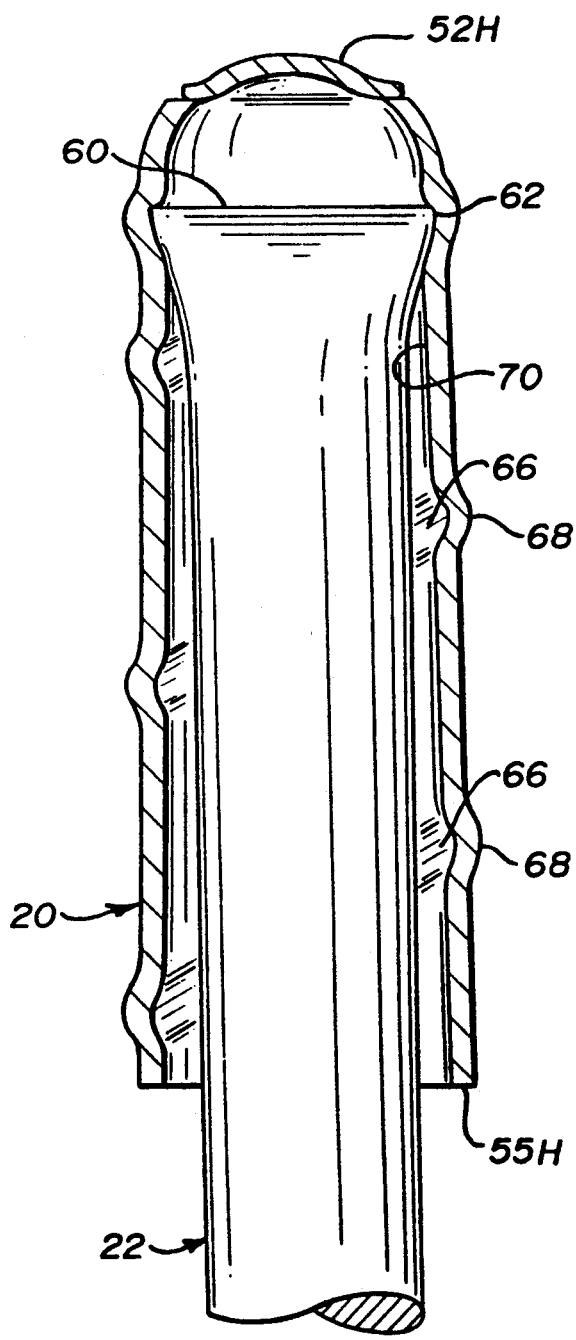

5,300,075

COVER FOR ORTHOPEDIC SPLINTING RODS AND METHOD OF INSTALLATION

BACKGROUND OF THE INVENTION

1. Field of the Invention

This invention relates to appliances for orthopedic surgery and more specifically to devices to cover the ends of splinting rods used to assist in the healing of bone fractures and the like.

2. Description of the Prior Art

Orthopedic splinting rods have gained wide application in orthopedic surgical procedures. Initially used for large fractures such as hip pinnings, these rods have become ever more frequently used and are now commonplace for many types of procedures seeking to properly set bone fragments o segments and fix the position of these segments during the knitting process. As these splinting rods have become ever more widely used, problems have been noticed with respect to the presence of the rod in the patient or extending out of the patient during the prolonged period of healing. The end of the rod is cut, often by clipping, to shape so as not to protrude for an extended length. But the end is often sharp and, if inside the body, can produce extensive trauma to surrounding tissues by causing lacerations and/or also acting as a site for infection. If the end of the rod is positioned outside the body as, for example, in the pinning of finger bones or toe bones, the ends of the rods can lacerate the surrounding tissue mass, such as adjoining fingers or toes, etc., and, again, are a hazard.

Many attempts have been made to provide appropriate covers for these types of splints, but none of them have been totally successful. An example of such a device is shown in U.S. Pat. No. 4,688,560 to Schultz.

The ideal device should be small, light, securely held to the end of the orthopedic splint and be easy to apply and difficult to remove. Many of the prior devices achieve some or many of these objectives. However, the cost and ease of manufacturing is another factor which has to be considered and simplicity of the product is also of paramount importance both from the standpoint of reliability, ease of application, and also from the aspect of per unit cost.

SUMMARY AND OBJECTS OF THE INVENTION

The present invention sets forth a cover for orthopedic splinting rods which in its broadest sense consists of a single sheet of material which is formed into a cylinder having a longitudinal slit up its side and a curved top of the cap to allow for natural resilience of the cap to hold the walls of the cap against the edges of the ends of the splinting rods to insure retention of the cap on the ends of the splinting rods. An embodiment for external use encases the metal cap in a plastic housing having a gripping means to assist in the installation of the cap on the ends of the splinting rod. The external housing has smooth surfaces to avoid and minimize any trauma to surrounding body tissue.

The present invention also sets forth a method of installing a cover for orthopedic splinting rods on the clipped end of the rod, comprising the steps of rotating of the metal cap down over the burred end of the clipped splinting rods and rotating the cap to cause the burred end of the cap to form a helical groove or type of screw thread in the wall of the cap to secure the cap. The cap tapers at the end near the top so as to cause ever increasing pressure on the burred end of the splinting rod as it is advanced into the cap.

Accordingly, it is an object of the present invention to provide a cover for orthopedic splinting rods which is easy to apply.

It is an another object of the present invention to provide a cover for orthopedic splinting rods which will adhere to the ends of the orthopedic splinting rods.

It is an yet another object of the present invention to provide a cover for orthopedic splinting rods which is relatively light.

It is still another object of the present invention to provide a cover for orthopedic splinting rods which is relatively simple to fabricate.

It is a further object of the present invention to provide a cover for orthopedic splinting rods which doesn't require elaborate tools to install or remove.

It is still a further object of the present invention to provide a cover for orthopedic splinting rods which is a relatively simple construction, which can be used with a range of sizes of splinting rods or wires.

It is yet another object of the present invention to provide a cover for orthopedic splinting rods which is provided with means to enable easy insertion by hand.

It is still another object of the present invention to provide a cover for orthopedic splinting rods which have external surfaces shaped to insure minimum trauma to surrounding body tissues.

Another object of the present invention is to provide a method for installation of orthopedic splinting rods, which tapers to increase the force necessary to dislodge the cap as the cap is advanced along the access of the wire.

Additionally, there's another object of the present invention to provide a method for installation of orthopedic splinting rods which enables the cover to be secured with ever greater force as it advances along the access of the rod at the end of the rod.

Still another object of the present invention is to provide a method for installation of orthopedic splinting rods which produces an effective threaded connection between the cap and the splinting rod after the cap is installed.

These, as well as further objects and advantages of this invention will become apparent to those skilled in the art from a review of the accompanying detailed description of the preferred embodiment, reference being made to the accompanying drawings.

BRIEF DESCRIPTION OF THE DRAWINGS

FIG. 7 shows a cover installed and positioned over the end of an orthopedic splinting rod.

FIG. 8 is a view along lines along 8—8 of FIG. 7.

DETAILED DESCRIPTION OF THE INVENTION

Figure 1:
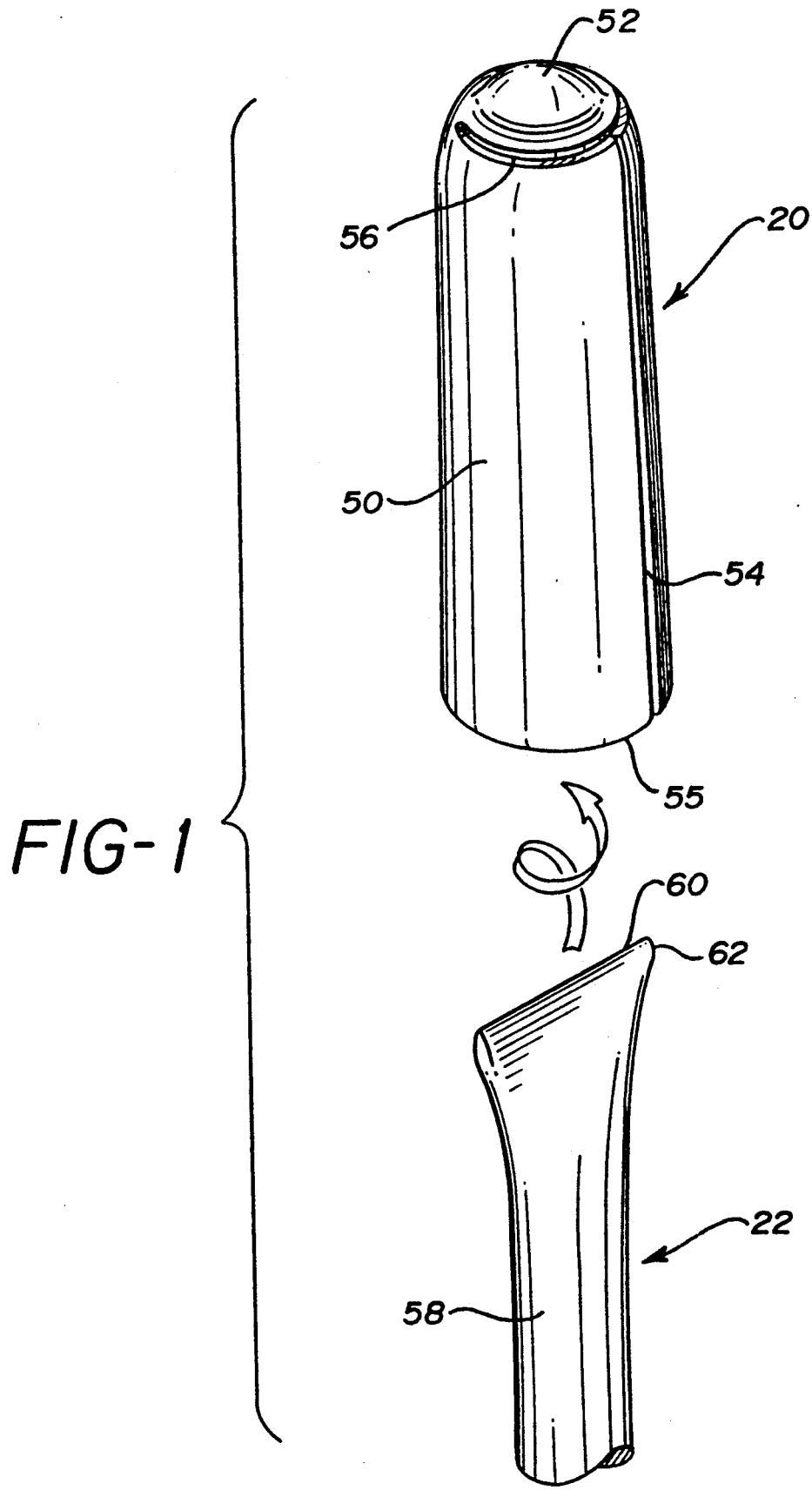
FIG. 1 is an exploded view showing the internal embodiment of a cover for an orthopedic cap built in accordance with the teaching of the present invention and the end of an orthopedic splinting rod or Kirshner wire in their appropriate relation prior to attachment of the cover.
Figure 2:
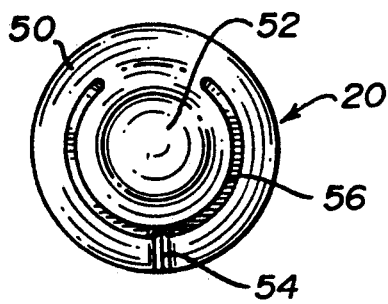
FIG. 2 is a top view of the cover shown in FIG. 1.
Figure 3:
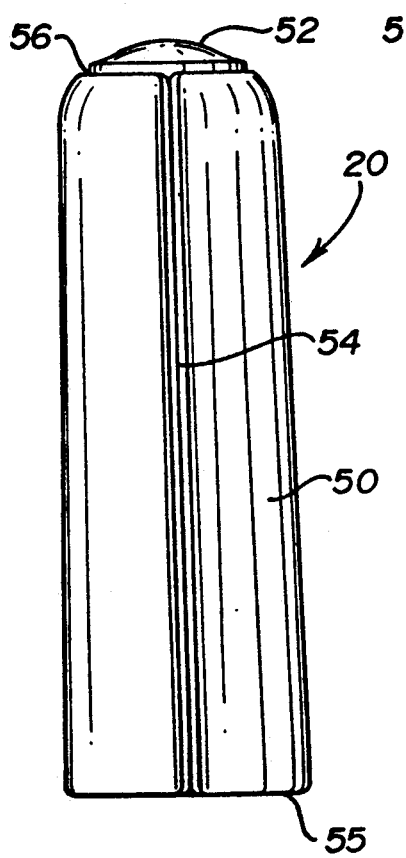
FIG. 3 is a front elevation of the cover shown in FIG. 1.
Figure 4:
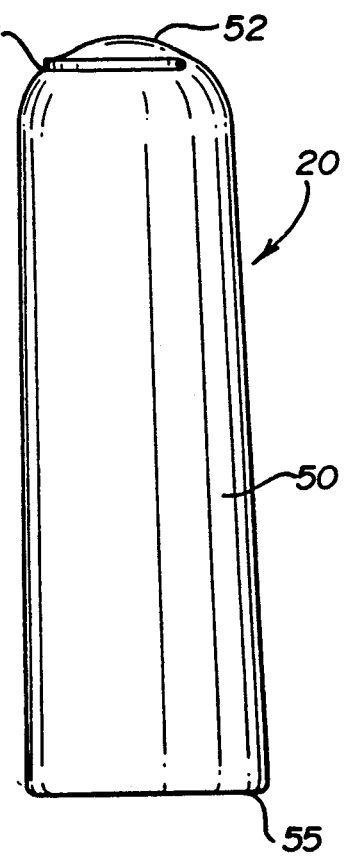
FIG. 4 is a right elevation of the cover shown in FIG. 1, which is a mirror image of the left elevation thereof.
Figure 5:
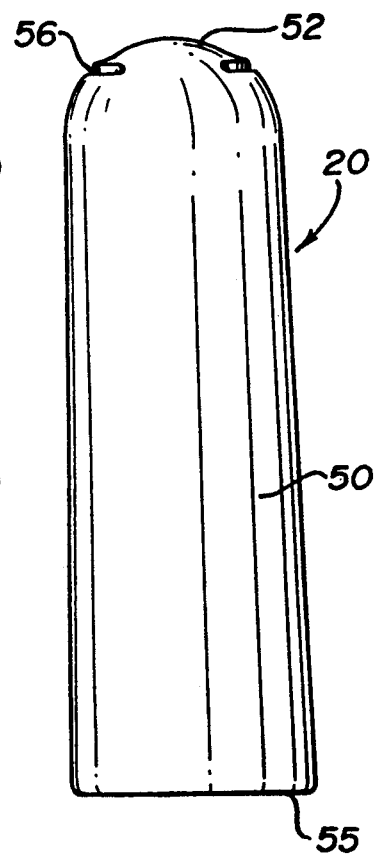
FIG. 5 is a rear elevation of the cover shown in FIG. 1.
Figure 6:
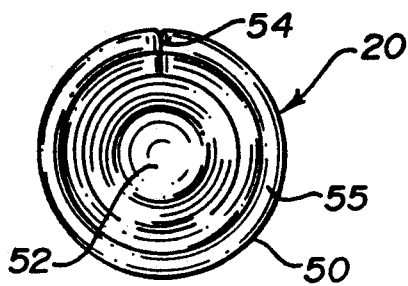
FIG. 6 is a bottom plan view of the cover shown in FIG. 1.

FIG. 1 generally shows a cover for an orthopedic splinting rod and a splinting rod separated prior to installing the cover on the end of the splinting rod. The cover, generally indicated at 20, has side walls 50 and a top portion 52. The cover is made from a single sheet of material 64 which has been rolled and stamped to form the walls 50 with the top 52 folded over. The ends of the walls are adjacent to each other and form a long slit 54 down the length of the cap, having a first side 54A and a second side 54B, the top being folded over has an extended top slit 56. The top slit is comprised of first and second slits extending from the opposing edges of the sheet of material at equal distances above the bottom edge and parallel to the bottom edge. The cap has a bottom edge 55.

The orthopedic splinting rod or wire or kirshner rod 22 has a shank generally indicated at 58 and an end 60 which been clipped as by a plier or the appropriate orthopedic tool, so that it has the approximate desired length to extend beyond the bone in which the rod is sitting. The rod, however, is clipped so as not to extend too long so as to cause the ends of the rod to be in contact with surrounding bodies and, therefore, apply forces to the bones that it is seeking to stabilize. When clipping the end of the rod, a burr 62 is formed, and this will have an edge caused by the normal ductility of the metal as it is squeezed to be clipped. The hardness of the rod is greater than that of the cap, so that when the cap is rotated over the burr at the end of the clipped rod, the burr will gouge a path or groove 66 in the inner wall 70 which gouging may be so large so as to form a ridge 68 in the outer wall not necessarily so. This can be seen in FIGS. 7 and 8 where 54H indicates the slit.

As shown most clearly in FIG. 8, the cap has an inner wall 70 and as can clearly be seen, the inner wall 70 tapers from the bottom 55H of the cap up to its top 52H and especially near the top of the cap where the end of the rod is shown. Therefore, when the bottom 55H of the cap or cover 20 is placed over the end of the end 60 of rod 22, it will fit fairly easily into the cover. The cover is then rotated and advanced downwardly on the end of the rod and the burred end will gouge the helical path previously described. The slit 54 in the side of the cap allows the natural resilience of the cap to come into play to allow the walls to expand slightly to receive the end of the rod as the cap is advanced downward on to the rod and, therefore, acts as a spring, in effect, to hold the cover in position on the rod.

Another way of describing the invention is a cover for an orthopedic splinting rod comprising a sheet of metal; said sheet of metal formed into a tapered, cylindrical body; the sheet having a top edge and a bottom edge and opposed extent edges; the sheet bent to position the opposed extent edges to closely abut along their entire length to form a slit along the length of the cylindrical body; the bottom edge formed to define a circle in a plain perpendicular to the longitudinal axis of the cover; the sheet also having a top portion formed in a spherical segment enfolded down over the ends of the tubular section to form a rounded top surface.

Additionally, included within the scope of this invention is a cover for an orthopedic splinting cap formed from a single sheet comprising a sheet of metal having a bottom edge and opposing side edges; a first and second slit extending from said opposing edges of said sheet of metal at equal distances above the bottom edge and parallel to the bottom edge thereof; the length of said slits being less than the width of said sheet; the portion of said metal sheet below said slits rolled into a tubular section; the portion above the slits formed into a spherical section; the material in said sheet between the ends of the slits acting as a hinge to bend over the spherical section to form a top for the tubular section.

ANOTHER EMBODIMENT

Referring to FIGS. 9-13, we see other embodiments of the invention including an external cover intended for external applications where the ends of the rod extend beyond or outside of the body. In contrast, the embodiment shown in FIGS. 1-8 shows a cover which has minimum volume and, therefore, is intended for applications where it must be attached to wires or splinting rods that ar totally maintained within the body.

Figure 9:
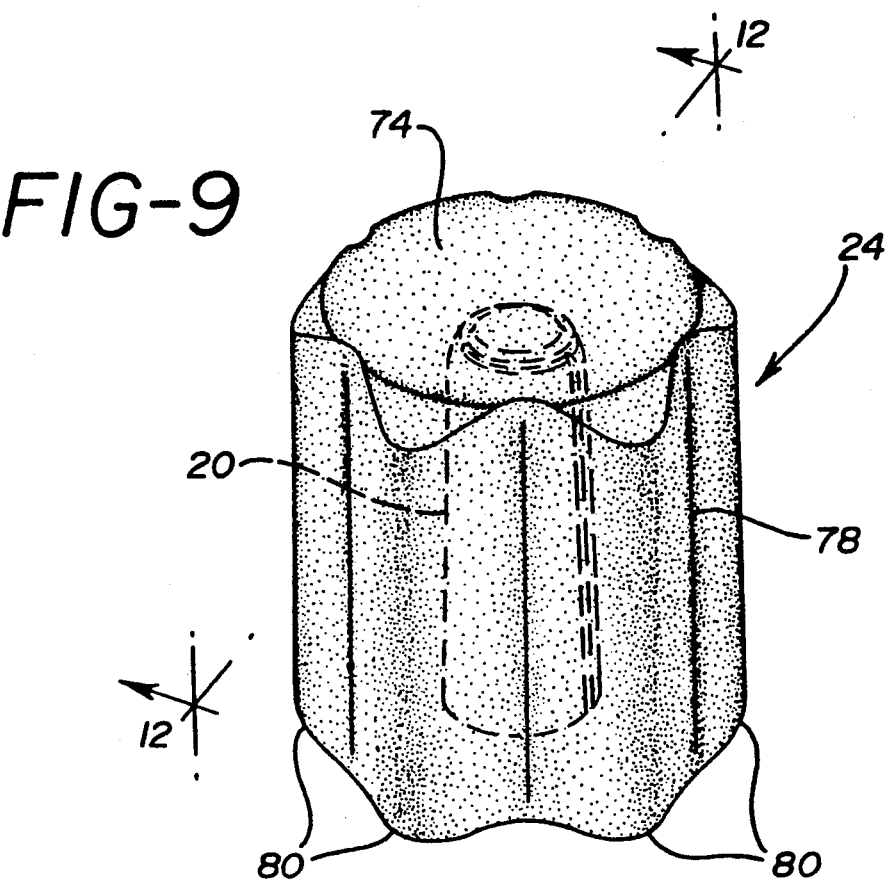
FIG. 9 is a perspective view of another embodiment of a cover for an orthopedic splinting rod intended for use external to the body.
Figure 10:
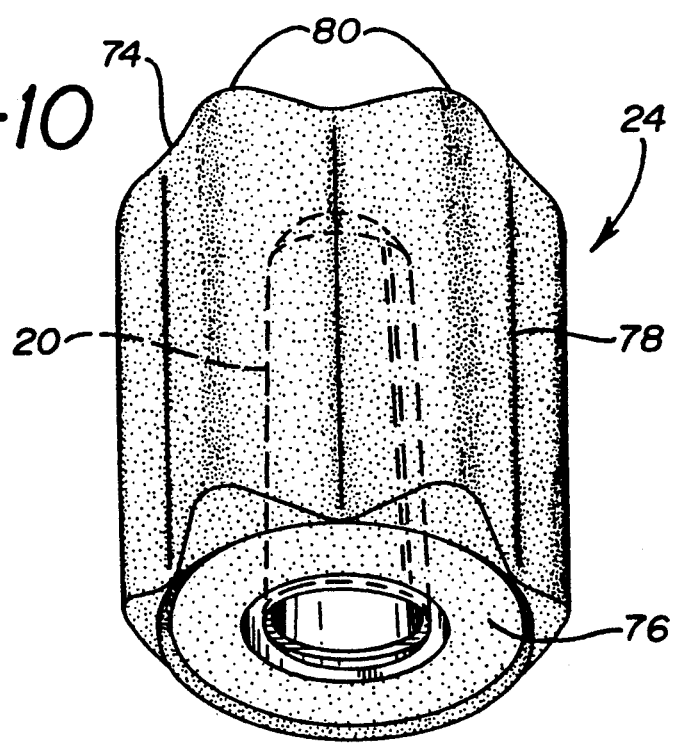
FIG. 10 is perspective from below of the device shown in FIG. 9.
Figure 11:
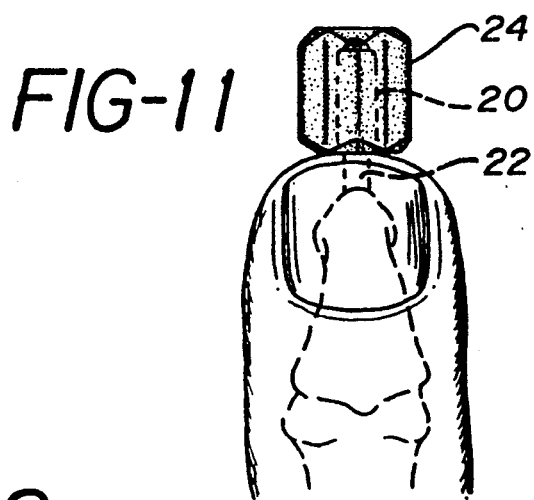
FIG. 11 shows a cover for an orthopedic splinting rod intended for external use in its environment, namely, on the end of a splinting rod extending from a finger bone.

The device shown in FIG. 9 contains the entire cover shown in FIGS. 1-6. However, the cover has been molded into a plastic outerbody of moderate resilience. Accordingly, the external cover generally indicated at 24 has a top 74 and a bottom 76 and sides 78. The sides have lobes 8 which extend out and provide gripping surfaces in order to attach the cap to the splinting rod. The top and bottom of the lobes have chamfers 82 to reduce and minimize any sharp edges that may be presented by the external cover.

Figure 12:
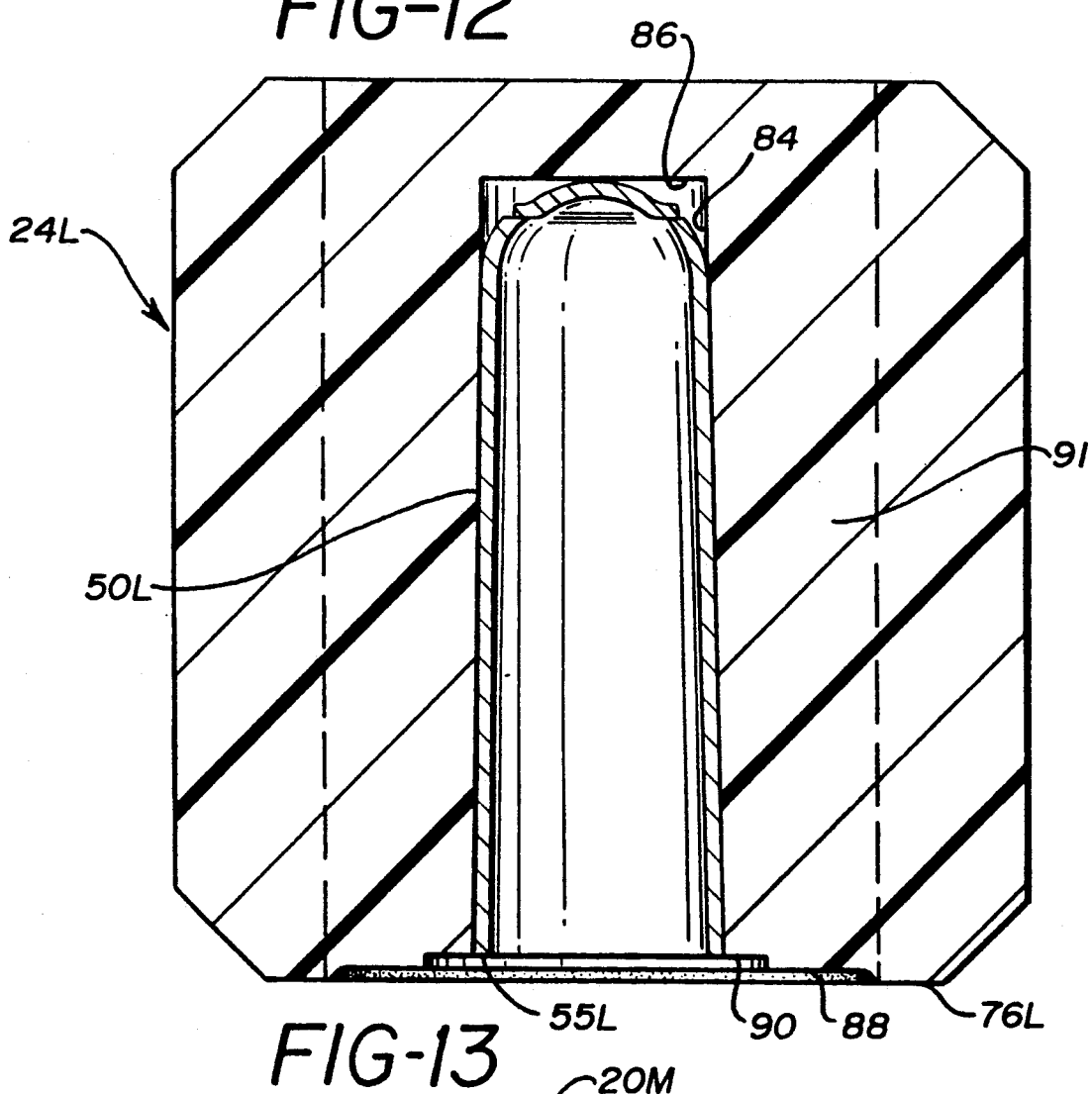
FIG. 12 is a view taken along lines 12—12 of FIG. 9.

As shown in FIG. 12, the walls of the cover 50L are positioned within the external cover in a cylindrical chamber having walls 84 and a top end 86. The bottom surface 76L of the external cap 24L has two steps, an outer step 88 and an inner step 90, for positioning the bottom 55L of the metal portion of the cover away from the bottom of the external cover generally.

The same principle of application applies to the external cover as with respect to the internal model, the only difference being that relatively thick walls 91 provide additional resilience to the walls 50L of the metal portion of the cover, so that a greater resilient force is exerted against the burred end of the rod or wire as the cover is advanced downward along the axis of the wire or rod. Note that because of the greater resilience provided by the walls 91, it would be possible to have perfectly parallel sides of the metal portion of the cover as shown in FIG. 12 as contrasted with the tapered sides as shown in FIGS. 1-8.

Figure 13:
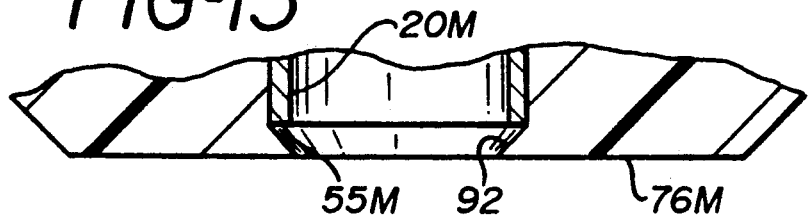
FIG. 13 is a partial sectional view, of another embodiment of the device, similar to that shown in FIG. 12, but with a modified bottom configuration.

FIG. 13 shows an embodiment somewhat different from that shown in FIG. 12 in that the bottom of the external cover instead of having a series of steps has a babbitt 92, or undercut, in the bottom 76M to hold the bottom edge 55M of the metal portion of the cover.

Having thus described my invention in detail, it is to be understood that the foregoing description is not intended to limit the spirit and scope thereof. What is desired to be protected by Letters Patent is set forth in the appended claims.

What is claimed is:

1. A cover for an orthopedic splinting rod comprising:
    said cover formed from a flat sheet of metal
    the sheet having a top edge and a bottom edge and opposed extent edges;
    said sheet of metal formed into a tapered, cylindrical body having an open end and a closed end;
    the sheet bent to position the opposed extent edges to coact to form a slit along the length of the cylindrical body;
    the bottom edge formed to define a circle in a plane perpendicular to the longitudinal axis of the cover;
    the sheet also having a top portion defined by at least one slit, the top portion formed in a spherical segment enfolded down over the ends of the cylindrical body to form a rounded top surface.

2. The apparatus of claim 1 wherein the cylindrical body tapers from the bottom edge to the top edge.

3. The apparatus of claim 1 further comprising an outer cover having an internal bore for receiving the cylindrical cover.

4. The apparatus of claim 3 wherein the outer cover comprises side walls having a plurality of lobes thereon to provide a gripping means.

5. The apparatus of claim 4 wherein the lobes have chamfers to reduce and minimize sharp edges.

6. The apparatus of claim 3 wherein the outer cover adds resiliency to the cylindrical cover.

7. The apparatus of claim 1 wherein the cylindrical body is substantially smooth.

8. A cover for an orthopedic splinting cap formed from a single sheet comprising:
    a sheet of metal having a bottom edge and opposing side edges;
    a first and second slit extending from said opposing edges of said sheet of metal at equal distances above the bottom edge and parallel to the bottom edge thereof;
    the length of said parallel slits being less than the width of said sheet;
    the portion of said metal sheet below said parallel slits rolled into a tubular section to form a cylindrical body the opposing side edges coacting to form a continuous slit along the length of the cylindrical body;
    the portion above the parallel slits formed into a spherical section;
    the material in said sheet between the ends of the parallel slits acting as a hinge, shorter in length that the diameter of said spherical section to bend over the spherical section to form a top for the tubular section.

9. The apparatus of claim 8 wherein the cylindrical body tapers from the bottom edge to the top edge.

10. The apparatus of claim 8 further comprising an outer cover having an internal bore for receiving the cylindrical metal cover.

11. The apparatus of claim 10 wherein the outer cover comprises side walls having a plurality of lobes thereon to provide a gripping means.

12. The apparatus of claim 11 wherein the lobes have chamfers to reduce and minimize sharp edges.

13. The apparatus of claim 10 wherein the outer cover adds resiliency to the cylindrical cover.

14. The apparatus of claim 8 wherein the cylindrical body is substantially smooth.

15. A cover for orthopedic splinting rods comprising:
    an inner covering comprising a sheet of metal;
    said sheet of metal formed into a tapered, cylindrical body;
    the sheet having a top edge and a bottom edge and opposed extent edges;
    the sheet bent to position the opposed extent edges to closely abut along their entire length to form a slit along the length of the cylindrical body;
    the bottom edge formed to define a circle in a plane perpendicular to the longitudinal axis of the cover;
    the sheet also having a top portion formed in a spherical segment enfolded down over the cylindrical body to form a rounded top surface;
    an outer cover having an internal cylindrical bore housing said inner covering, the external cover having a top surface and a bottom surface and having wall surfaces;
    said wall surfaces having a plurality of lobes thereon to provide a gripping means.

16. The apparatus of claim 15 wherein the outer cover has a series of steps formed at its bottom surface.

17. The apparatus of claim 15 wherein a babbitt is formed in the bottom surface of the outer cover to hold the bottom edge of the inner covering.

18. The apparatus of claim 15 wherein the lobes have chamfers to reduce and minimize sharp edges.

19. The apparatus of claim 15 wherein the outer cover adds resiliency to the cylindrical body.

20. A method of inserting a cover onto a burred edge of a splinting rod comprising:
    positioning a cylindrical section over the burred edge of a splinting wire or rod to cover the burred edge of the splinting wire or rod, the cylindrical section having an open end and a closed end, the closed end smaller than the open end;
    advancing the cover axially along the wire or rod until contact is made with the burred end and the inner wall of the cover;
    rotating the cover about the burred end of the wire or rod and advancing the cover while rotating the cover to form a helical path; and
    gouging a helical path in the wall of the cover by advancing the cover over the burred end of the wire or rod to form a helical thread on the internal wall of the cover.

21. A cover for orthopedic splinting rods comprising:
    an inner cover comprising a sheet of metal;
    said sheet of metal formed into a cylindrical body having walls;
    the sheet having a top edge and a bottom edge and opposed extent edges;
    the sheet bent to position the opposed extent edges to closely abut along their entire length to form a slit along the length of the cylindrical body;
    the bottom edge formed to define a circle in a plane perpendicular to the longitudinal axis of the cover;
    the sheet also having a top portion formed in a spherical segment enfolded down over the cylindrical body to form a rounded top surface;
    an outer cover having an internal cylindrical bore housing said inner cover, the external cover having a top surface and a bottom surface and having wall surfaces;
    said outer cover providing a resilient force against expansion of said cylindrical body; and
    said wall surfaces having a plurality of lobes thereon to provide a gripping means.

22. The apparatus of claim 21 wherein the walls of the cylindrical body are parallel.

* * * * *